United States Patent [19]

Lamont

[11] Patent Number: Plant 7,544

[45] Date of Patent: Jun. 4, 1991

[54] *ANIGOZANTHOS* HYBRID VARIETY 'FIREFLY'

[75] Inventor: Gregory P. Lamont, Wyoming, Australia

[73] Assignee: Ornamental Native Australian Plants Pty Ltd, Armidale, Australia

[21] Appl. No.: 427,592

[22] Filed: Oct. 27, 1989

[30] Foreign Application Priority Data

Oct. 31, 1988 [AU] Australia ..... 88/031

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Ernest M. Anderson

[57] ABSTRACT

A new and distinct variety of *Anigozanthos* hybrid characterized by the combination of: arching leaves; average flowering stem length of 28 cm; a flower with a yellow-green perianth flaring distally; a yellow ovary covered with red hairs and a style ending below the anthers; and comes into flower all year round when propagated by tissue culture.

2 Drawing Sheets

ORIGIN OF THE VARIETY

This variety arises from the selection of a plant from seedlings grown at the Horticultural Research Station, Gosford New South Wales Australia. The exact parentage is not known but is believed to be a hybrid between *Anigozanthos bicolor* and *A. humilis*. The criteria for selection were flower color, flowering duration, growth habit and stem length. Subsequent plants have been propagated from that seedling by tissue culture. The subsequent plants produced possess all the characteristics or come true to form with the original plant and the characteristic features are firmly fixed and maintained in the succeeding generations of plants.

SUMMARY OF THE VARIETY

"Firefly" is a compact, dwarf herbaceous plant that is an average height of 28 cm. The flower has yellow green perianths and a yellow ovary clad in red hairs. The perianth flares distally and the style end below the anthers. The leaves are grasslike and arching. This variety commences flowering from tissue culture all year round. "Firefly" is suitable as a potted flowering ornamental plant.

DESCRIPTION OF PHOTOGRAPHS

The accompanying photographs show typically:

(i) the plant form and size and the display of flowers;
(ii) the relative size and color of the perianth of "Firefly" (middle), "Pixie Paw" (right) and *A. bicolor* (left).

The colors are a nearly true as reasonably possible in color representations of this type.

DESCRIPTION OF THE VARIETY

In the following botanical description color references are made to the Royal Horticultural Society Colour Chart. Descriptions are based on observations made during September 1988 of 20 randomly selected well fertilized, six-month old specimens grown in a cool greenhouse in Central Coastal New South Wales Australia under 20% shaded nursery conditions. The temperature ranged from about 8° C. to 20° C. in winter and 18° C. to 35° C. in summer.

DESCRIPTION OF THE VARIETY

Name: Kangaroo Paw "Firefly".

Botanical name: *Anigozanthos* hybrid. Family Haemodoraceae.

Commercial use: Potted flowering ornamental plant.

Form: Compact, dwarf herbaceous plant with grass-like arching leaves and furry-stemmed flowering heads.

Plant characteristics:

*Height.*—Mean 28.1 cm; Range 18 cm–37.0 cm.

*Leaf.*—Length: Mean 14.2 cm; Range 11–16 cm. Width: Mean 5.0 mm; Range 3.5–7.0 mm. Attitude: Arching. Color: 137A green. Margins: Pubescent.

*Flowering season.*—Comes into flower all year round when propagated using tissue culture.

*Anther position.*—Lateral rows (three levels).

*Floral tube outline.*—Flared distally.

*Perianth.*—Length: Mean 39.7 mm; Range 38.5–43.4 mm. Width: Mean 10.9 mm; Range 10.0–12.4 mm. Lobes: Fully reflexed.

*Flowers per inflorescence.*—Mean 17.65; Range 10–28.

*Inflorescence per plant.*—Mean 17.4; Range 10–33.

*Style length.*—Much shorter than anthers.

*Color.*—Of opened flower tube: 151A green. Of hairs of tube: 202A black. Of ovary: 17B yellow. Of hairs on ovary: 46A red.

COMPARISONS WITH OTHER KNOWN KANGAROO PAWS

*Anigozanthos* "Pixie Paw" is the only known dwarf (less than 30 cm height) Kangaroo Paw sold in Australian thus a comparison is made with this variety.

"Firefly" has longer flowering stems than "Pixie Paw"; 28.1 cm vs. 10.3 cm.

"Firefly" has a longer perianth tube; 39.7 mm vs. 25.4 mm.

"Firefly" has a wider perianth tube; 10.9 mm vs. 7.7 mm.

Color of opened flower:

| | "Firefly" | "Pixie Paw" |
|---|---|---|
| ovary | 17B yellow/orange | 53A red |
| ovary hairs | 46A red | 53A red |

-continued

| | "Firefly" | "Pixie Paw" |
|---|---|---|
| tube | 15A yellow green | 143C green |
| tube hairs | 202A black | 143C green |

The anthers of "Firefly" are at two levels, vs. three levels.

The style of "Firefly" is shorter than anthers, vs. style level with anthers.

The leaves of "Firefly" are strongly arching as compared with upright.

The leaf margins of "Firefly" are pubescent as compared with smooth or very slightly pubescent.

The length of leaf blades of "Firefly" are 14.2 cm vs. 5.4 cm.

The new variety is easy to propagate using tissue culture methods. Rooted plants may be hardened from tissue culture under intermittent mist and 60–80% shade for two weeks. Plants then reach flowering in 10–14 weeks when grown in a greenhouse under 80% full sunlight and a mean ambient temperature of about 22° C.

I claim the following:

1. A new and distinct cultivar of *Anigozanthos* hybrid known by the cultivar name "Firefly" and characterized as to uniqueness by the combined characteristics of arching leaves, average flower stem length of 28 cm, a flower with a yellow-green perianth flaring distally, a yellow ovary covered with red hairs and a style ending below the anthers and comes into flower all year round when propagated from tissue culture.

* * * * *

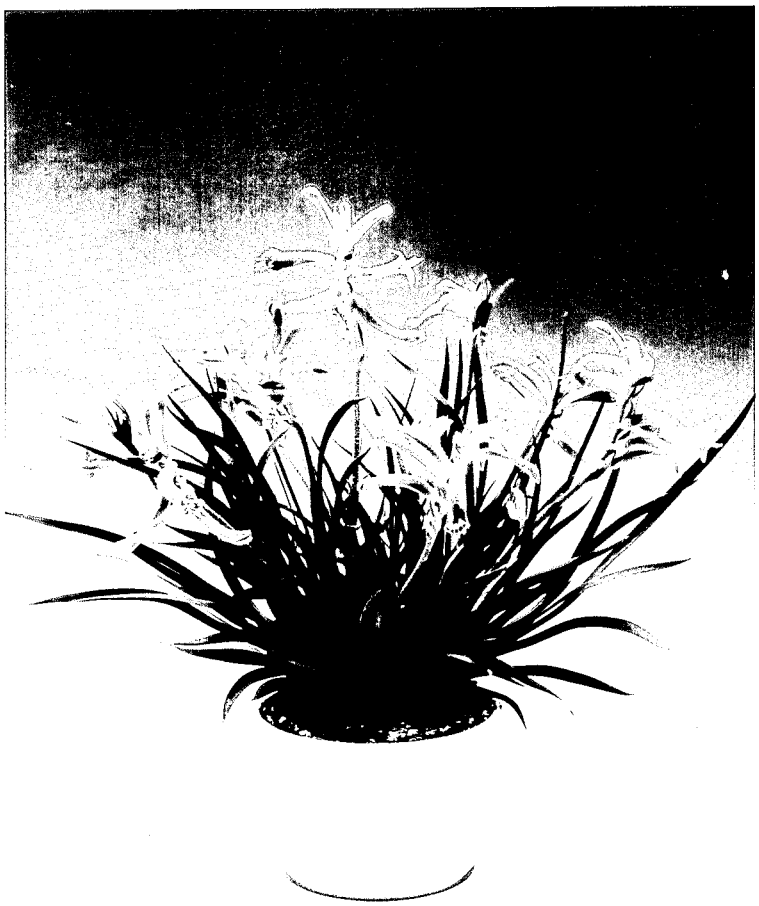
i)

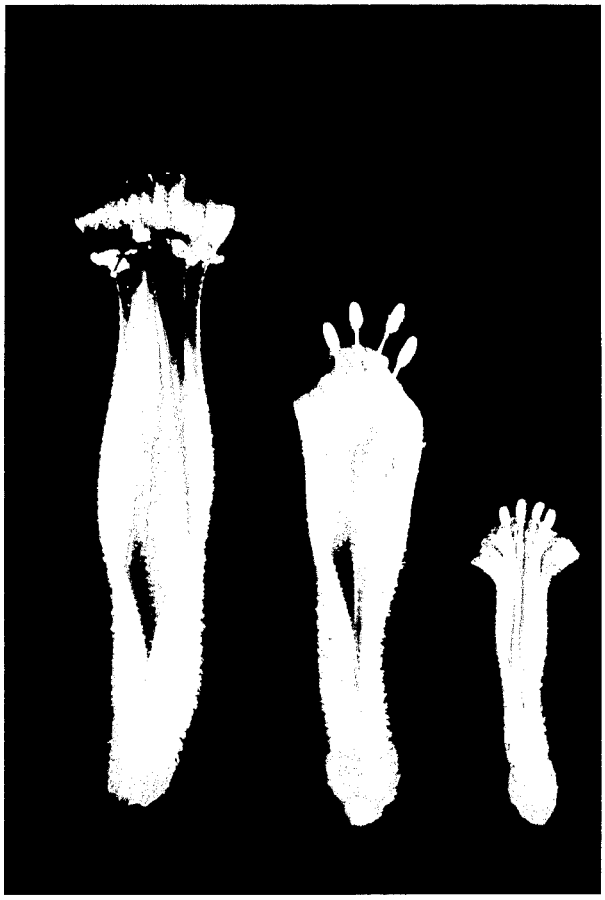
ii)